(12) United States Patent
Fridag et al.

(10) Patent No.: US 9,428,433 B2
(45) Date of Patent: Aug. 30, 2016

(54) CONTROL OF THE VISCOSITY OF REACTION SOLUTIONS IN HYDROFORMYLATION PROCESSES

(71) Applicants: Dirk Fridag, Haltern am See (DE); Udo Lenz, Recklinghausen (DE); Hans-Gerd Lueken, Marl (DE); Robert Franke, Marl (DE); Markus Rudek, Bonn (DE); Klaus-Diether Wiese, Haltern am See (DE); Soenke Broecker, Ober-Ramstadt (DE); Markus Priske, Mobile, AL (US); Christoph Patalong, Castrop-Rauxel (DE)

(72) Inventors: Dirk Fridag, Haltern am See (DE); Udo Lenz, Recklinghausen (DE); Hans-Gerd Lueken, Marl (DE); Robert Franke, Marl (DE); Markus Rudek, Bonn (DE); Klaus-Diether Wiese, Haltern am See (DE); Soenke Broecker, Ober-Ramstadt (DE); Markus Priske, Mobile, AL (US); Christoph Patalong, Castrop-Rauxel (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/653,717

(22) PCT Filed: Dec. 9, 2013

(86) PCT No.: PCT/EP2013/075933
§ 371 (c)(1),
(2) Date: Jun. 18, 2015

(87) PCT Pub. No.: WO2014/095452
PCT Pub. Date: Jun. 26, 2014

(65) Prior Publication Data
US 2015/0299079 A1    Oct. 22, 2015

(30) Foreign Application Priority Data
Dec. 18, 2012 (DE) .......................... 10 2012 223 572

(51) Int. Cl.
*C07C 45/50* (2006.01)
*B01J 19/00* (2006.01)
*B01J 19/24* (2006.01)

(52) U.S. Cl.
CPC .................. *C07C 45/50* (2013.01); *B01J 19/24* (2013.01); *B01J 2219/00162* (2013.01); *B01J 2219/00245* (2013.01); *B01J 2219/24* (2013.01)

(58) Field of Classification Search
CPC ........ C07C 45/50; B01D 19/24; B01D 61/00
USPC ................................. 568/451, 454; 422/187
See application file for complete search history.

(56) References Cited

U.S. PATENT DOCUMENTS

| | | | |
|---|---|---|---|
| 5,364,950 A * | 11/1994 | Babin | B01J 31/185 556/2 |
| 5,773,667 A | 6/1998 | Bahrmann et al. | |
| 6,482,992 B2 | 11/2002 | Scholz et al. | |
| 6,500,991 B2 | 12/2002 | Wiese et al. | |
| 6,555,716 B2 | 4/2003 | Protzmann et al. | |
| 6,960,699 B2 | 11/2005 | Tötsch et al. | |
| 7,138,552 B2 | 11/2006 | Kaizik et al. | |
| 7,154,012 B2 | 12/2006 | Lueken et al. | |
| 7,179,947 B2 | 2/2007 | Lueken et al. | |
| 7,193,116 B2 | 3/2007 | Moeller et al. | |
| 7,232,931 B2 | 6/2007 | Toetsch et al. | |
| 7,317,130 B2 | 1/2008 | Moeller et al. | |
| 7,323,586 B2 | 1/2008 | Wiese et al. | |
| 8,129,571 B2 | 3/2012 | Lueken et al. | |
| 8,138,379 B2 | 3/2012 | Lueken et al. | |
| 8,226,829 B2 | 7/2012 | Wiese et al. | |
| 8,389,774 B2 | 3/2013 | Becker et al. | |
| 8,404,902 B2 | 3/2013 | Kreidler et al. | |
| 8,415,520 B2 | 4/2013 | Winterberg et al. | |
| 8,461,394 B2 | 6/2013 | Lueken et al. | |
| 8,748,643 B2 | 6/2014 | Priske et al. | |
| 8,969,628 B2 | 3/2015 | Priske et al. | |
| 8,999,038 B2 | 4/2015 | Ungerank et al. | |
| 2007/0135665 A1 | 6/2007 | Wiese et al. | |
| 2008/0251456 A1 | 10/2008 | Wiese et al. | |
| 2009/0032465 A1 | 2/2009 | Baumgarten et al. | |
| 2012/0123079 A1 | 5/2012 | Ungerank et al. | |
| 2012/0279922 A1 | 11/2012 | Haensel et al. | |
| 2014/0343327 A1 | 11/2014 | Hamers et al. | |
| 2015/0018576 A1 | 1/2015 | Baumgarten et al. | |

FOREIGN PATENT DOCUMENTS

| | | |
|---|---|---|
| EP | 0 823 282 A2 | 2/1998 |
| EP | 1 931 472 B1 | 1/2009 |

OTHER PUBLICATIONS

U.S. Appl. No. 14/890,821, filed Nov. 12, 2015, Priske, et al.
U.S. Appl. No. 14/770,525, filed Aug. 26, 2015, Lueken et al.
International Search Report Issued Jun. 10, 2014 in PCT/EP13/075933 Filed Dec. 9, 2013.
U.S. Appl. No. 14/435,052, filed Apr. 10, 2015, Fridag, et al.

* cited by examiner

*Primary Examiner* — Sikarl Witherspoon
(74) *Attorney, Agent, or Firm* — Oblon, McClelland, Maier & Neustadt, L.L.P.

(57) ABSTRACT

The present invention relates to a method and a device for controlling the viscosity of reaction solutions in the hydroformylation of olefin-containing mixtures.

9 Claims, 8 Drawing Sheets

CONTROL OF THE VISCOSITY OF REACTION SOLUTIONS IN HYDROFORMYLATION PROCESSES

CROSS-REFERENCE TO RELATED APPLICATIONS

This application is a National Stage of PCT/EP2013/075933 filed on Dec. 9, 2013. This application is based upon and claims the benefit of priority to German Application No. 10 2012 223 572.8 filed on Dec. 18, 2012.

The present invention relates to a method of controlling the viscosity of reaction solutions in hydroformylation processes in which catalytically active compositions based on transition metal complex catalysts, in particular rhodium complex catalysts, are present in dissolved form.

The reactions between olefin compounds, carbon monoxide and hydrogen in the presence of a catalyst to form the aldehydes having one more carbon atom is known as hydroformylation or the oxo process. In the catalytically active compositions, compounds of the transition metals of group VIII of the Periodic Table of the Elements are frequently used as transition metal complex catalysts in these reactions.

Known ligands in these catalytically active compositions are, for example, compounds from the classes of phosphines, phosphites, phosphinites, phosphoramidites and phosphonites, each containing trivalent phosphorus $P^{III}$.

A good overview of the prior art for hydroformylation of olefins may be found in B. Cornils, W. A. Herrmann, "Applied Homogeneous Catalysis with Organometallic Compounds", Vol. 1 & 2, VCH, Weinheim, New York, 1996, or R. Franke, D. Selent, A. Barrier, "Applied Hydroformylation", Chem. Rev., 2012, DOI:10.1021/cr3001803.

A classical application is the production of C5-aldehydes by hydroformylation of unsaturated C4 compounds which are obtained in petrochemical processing plants. Industrially available starting materials of this type are hydrocarbon mixtures which contain 1-butene, (cis- and trans-) 2-butene, isobutene and multiply unsaturated and saturated hydrocarbons.

The catalyzed hydroformylation of olefins to form the corresponding aldehydes is usually carried out in a homogeneous, liquid phase, i.e. olefin and products are present in one phase, with the catalytically active composition being homogeneously dissolved in the liquid reaction mixture.

In addition, an inert solvent for the catalytically active composition can be present in the reaction mixture.

As products of the hydroformylation, not only the said aldehyde as primary product but also higher-boiling subsequent products (usually referred to as high boilers) are typically formed as primary product; see Rhodium-catalyzed Hydroformylation, ed. by P. W. N. M. van Leeuwen and C. Claver, Kluwer Academic Publishers 2006, AA Dordrecht, NL, pages 206-211. Here, not only high boiler formation but also removal of the high boilers and catalyst poisons from the catalyst solution by distillation are described. The combustion of the rhodium-containing residues is also indicated here as an alternative route.

For the present purposes, "high boilers" are materials which boil at a higher temperature and have higher molar masses than the primary hydroformylation product (aldehyde having one more carbon atom than the olefin used) and the alcohol obtained therefrom by hydrogenation. High boilers are formed by subsequent reactions of the primary hydroformylation product. High boilers typically formed in industrial hydroformylation include aldolization products and acetalization products and also esters formed by reaction of alcohols and acids, with the alcohols and acids being formed, in particular, by disproportionation of aldehydes.

An industrial hydroformylation typically gives a product mixture which comprises the primary product n-aldehyde, subsequent products in the form of high boilers and the transition metal complex catalyst and the free ligands thereof. Depending on the conversion in the reaction, the product mixture taken off from the reactor can also contain unreacted starting material, i.e. olefin, hydrogen or carbon monoxide.

To increase the purity of the primary product and recover the catalytically active composition, it is necessary to separate the constituents aldehyde, subsequent products and transition metal complex catalyst and any unreacted starting materials present in the product mixture obtained in the hydroformylation from one another.

DE 10 2008 002 187 A1 describes a rhodium-containing catalytically active composition containing a biphosphite ligand with addition of a stabilizer for the hydroformylation of C4 streams. The product is removed from the reaction solution by means of a classical stripping gas stream and is subsequently condensed out.

This document also reports the formation of insoluble subsequent products of the ligand which are removed from the reaction solution by means of filtration.

WO 2010/003073 describes a separation of the high boilers from a hydroformylation process by means of a gas stripping process which is operated in such a way that the reaction mixture from the reaction is passed to a thermal work-up in order to remove proportions of both the products and the high boilers from the reaction mixture with the aid of a stripping gas.

This process is only able to remove components from the system according to their boiling point.

In EP 1931472 B1, a membrane filtration is used for separating off rhodium complex catalysts before a thermal work-up. In this thermal separation, the high boiler stream is likewise worked up once again by means of a membrane and a high boiler stream is discharged. The retentate stream from the second membrane plant is recirculated to the reaction.

In EP 1 232 008, the reaction mixture is depressurized and admixed with a diluent before the membrane filtration in order to prevent blocking of the membrane.

EP1931472B1 describes organophilic nanofiltration for separating homogeneously dissolved catalyst complexes from hydroformylation mixtures.

The catalytically active composition, in particular the phosphide ligands, used in the hydroformylation can be degraded in various ways.

U.S. Pat. Nos. 5,364,950 and also 5,763,677 and "Catalyst Separation, Recovery and Recycling", edited by D. J. Cole-Hamilton, R. P. Tooze, 2006, NL, pages 25-26, describe the formation of "Poisoning Phosphites" as secondary or ligand degradation reaction. These "Poisoning Phosphites" are formed during the hydroformylation reaction when using aryl phosphite-modified rhodium complexes. In the course of the degradation of the ligands in the catalytically active composition, an aryl group is replaced by an alkyl group of the hydroformylation product.

The phosphite ligands can also be degraded in a hydrolysis reaction by the traces of water formed in the aldehyde condensation (high boiler formation), see Paul C. J. Kamer, Joost N. H. Reek and Piet W. N. M van Leeuwen in "Rhodium Catalysed Hydroformylation" Volume 22, page 44. A consequence of these degradation reactions of the ligands is that the concentration of hydroformylation-active rhodium complex species decreases over the course of time and is associated with a decrease in reactivity. It is generally catalytically active in the hydroformylation and degradation products of the composition which is catalytically active in the hydroformylation.

D. R. Bryant in "Catalyst Separation, Recovery and Recycling" Springer 2006, in Chapter 2 2.6.1.6 to 2.6.1.8, reports the hydrolysis of the phosphites via various intermediates.

The following scheme shows the degradation products formed from the ligand known as biphephos for short (6,6'-((3,3'-di-tert-butyl-5,5'-dimethoxy-[1,1'-biphenyl]-2, 2'-diyl)bis(oxy))bisdibenzo[d,f][1,3,2]dioxaphosphepine). Intermediates are not incorporated in this scheme and hydrolytic degradation is assumed.

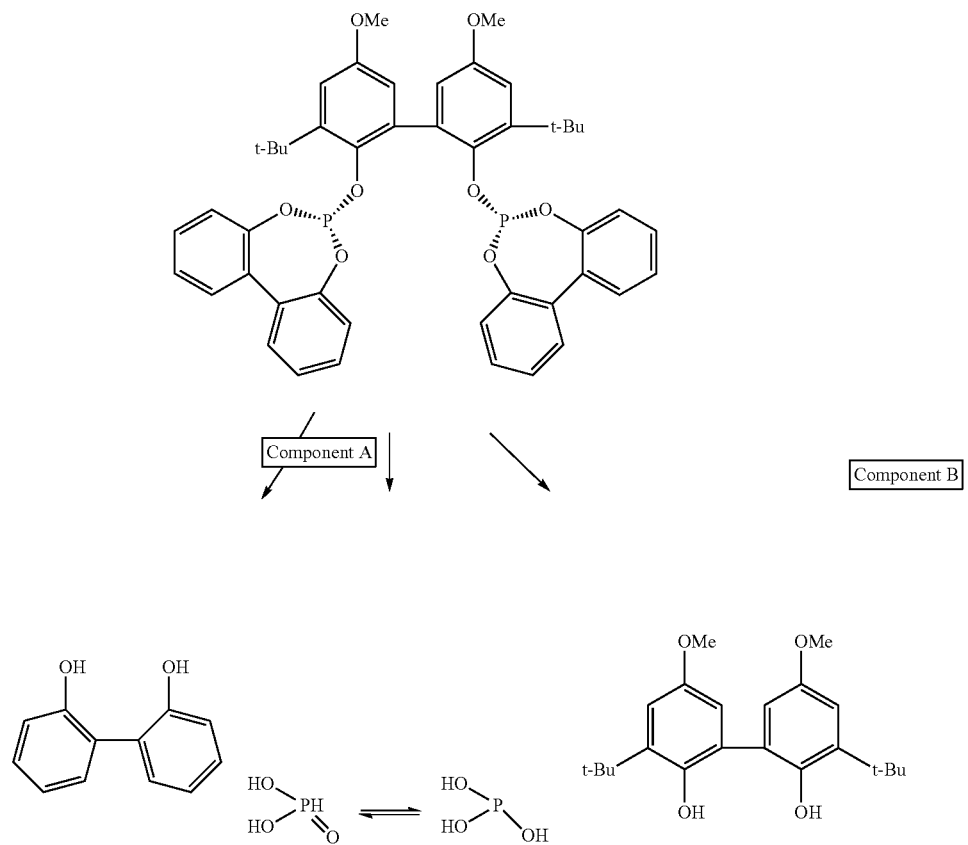

known that in a continuous hydroformylation process, further ligand(s) and optionally further components have to be introduced during the course of the reaction, i.e. have to be additionally added after commencement of the reaction (see DE 10 2008 002 187 A1).

Although the stability can be improved by appropriate modification of the ligand, degradation of the composition which is catalytically active in the hydroformylation, in particular the ligands used, cannot be prevented entirely. In the remainder of the present patent application, the terms ligand degradation and ligand degradation products are used as equivalent to degradation of the composition which is The components A, viz. 2,2'-biphenol, and B, viz. 3,3'-di-tert-butyl-5,5'-dimethoxy(1,1'-biphenyl)-2,2'-diol, were able to be detected analytically (NMR).

The hydrolysis of the phosphite ligands is likewise described in "Homogeneous Catalysts: Activity—Stability—Deactivation, First Edition". Piet W. N. M. van Leeuwen and John C. Chadwick.

The documents indicate, for example, the following phosphites which are subject to an identical chemical degradation mechanism and thus lead to corresponding alcohols, diols and possibly carboxylic acid derivatives, in particular phenols, biphenols, binaphthols.

Ligand 5 b

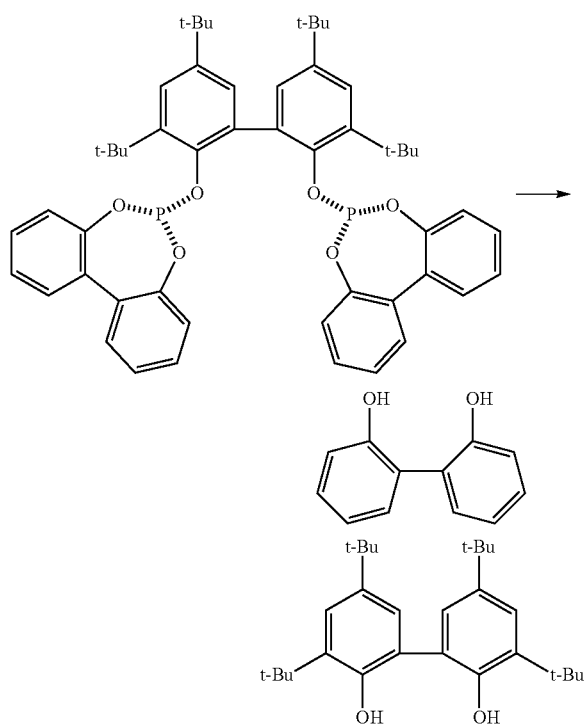

Gladfelter ligand ("Rhodium Catalysed Hydroformylation") page 54

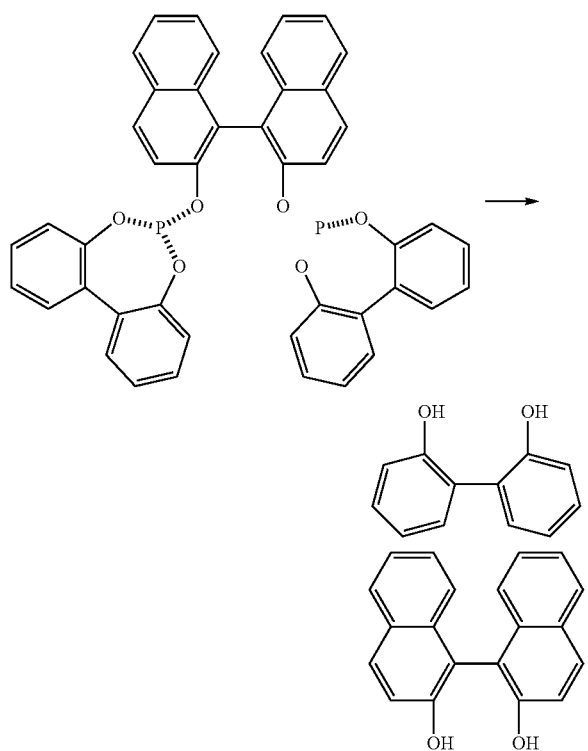

Mitsubishi ligand ("Rhodium Catalysed Hydroformylation") page 58

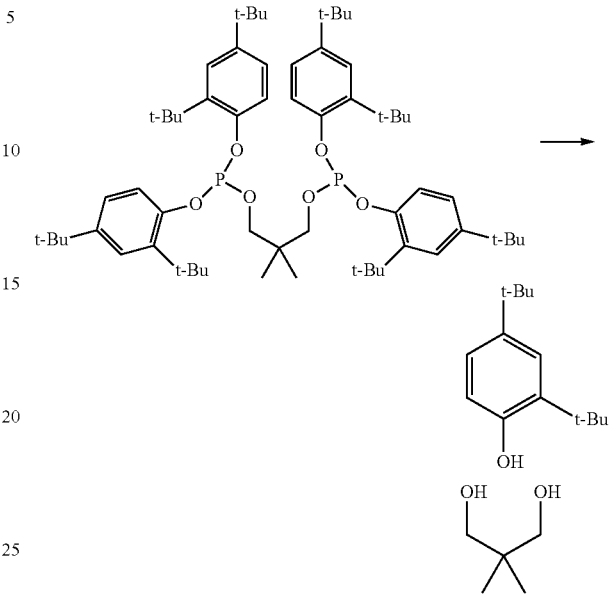

These various ligand fragments and ligand degradation products cannot be separated off by the methods previously described in the prior art. Accumulation of these degradation products therefore occurs.

This accumulation of the degradation products leads to a significant rise in the viscosity of the reaction solution. Such a viscosity rise generally leads to mass transfer problems which in turn lead to a decrease in the total activity of the process.

The formation of solids as described in DE 10 2008 002 187 A1 leads to an increased outlay since these filters have to be cleaned and replaced at regular intervals.

Proceeding from this prior art, it is an object of the present invention to keep the viscosity of the reaction solution constant over long periods of time and thus avoid formation of solids and also a decrease in reactivity.

It has surprisingly been found that when the reaction products are separated off via the gas phase by means of their respective partial pressures, the viscosity of the reaction solution can be kept constant over long periods of time by passing in a "stripping gas" and discharging the ligand degradation products formed from the ligands used and also recirculating the composition which is catalytically active in hydroformylation by means of membrane filtration. The formation of solid, as is described in DE 10 2008 002 187 A1, no longer occurs.

Figure 1:
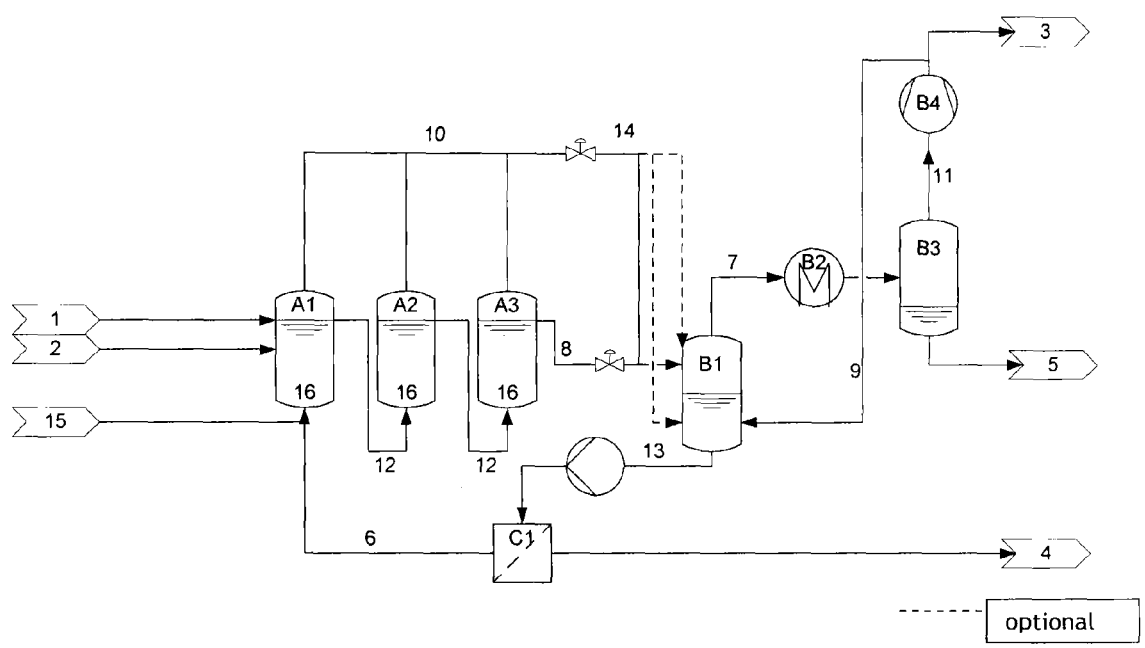
FIG. 1 is a schematic diagram of an embodiment of the apparatus of the invention.

The present invention provides:

1.) a method of controlling the viscosity of reaction solutions in the hydroformylation of olefin-containing mixtures, which comprises the steps:
i) providing a mixture containing saturated and olefinically unsaturated hydrocarbons, a composition which is catalytically active in hydroformylation, a gas mixture composed of carbon monoxide and hydrogen and at least one solvent;
ii) contacting the starting materials in at least one reaction zone;
iii) separating off the products, with a gas stream containing a mixture of saturated and olefinically unsaturated hydrocarbons, carbon monoxide and hydrogen being introduced into at least one reaction zone, with the proviso that the products are discharged via the gas phase from the reaction zone;
iv) condensing the products which have been separated off via the gas phase and passing them to further work-up;
v) passing the bottom stream from at least one reaction zone to at least one membrane filtration, characterized in that the composition which is catalytically active in hydroformylation is retained via the retentate and recirculated to the reaction zone and degradation products of the composition which is catalytically active in hydroformylation are removed via the permeate;

and also

2.) an apparatus for controlling the viscosity of reaction solutions in the hydroformylation of olefin-containing mixtures, which comprises:
i) at least one reaction zone;
ii) compressor;
iii) pressure regulator;
iv) at least one condensation zone which comprises a heat exchanger and downstream collection vessels;
v) at least one membrane filtration, characterized in that the degradation products of the composition which is catalytically active in hydroformylation is separated off via the permeate from the reaction mixture and the composition which is catalytically active in hydroformylation is retained via the retentate and recirculated to the reaction zone.

An embodiment of the method of the invention comprises, as composition which is catalytically active in hydroformylation:
a) at least one organophosphorus compound containing trivalent phosphorus;
b) at least one metal of groups 8-10 of the Periodic Table of the Elements;
c) optionally a stabilizing component.

In a particular embodiment of the process of the invention, the organophosphorus compound containing trivalent phosphorus is selected from among phosphines, phosphites, phosphonites, phosphinites, phosphoramidites, the metal is selected from group 8 of the Periodic Table of the Elements, and the stabilizing component is selected from among sterically hindered amines.

In a very particular embodiment of the method of the invention, the metal is rhodium and the sterically hindered amine comprises at least one 2,2,6,6-tetramethylpiperidine unit.

In an embodiment of the method of the invention, the degradation products of the composition which is catalytically active in hydroformylation, selected from among alcohols, phenols, diols, in particular biphenols, binaphthols, are removed via the permeate.

In a further embodiment of the method of the invention, the membrane filtration is carried out:
1) in a temperature range of 20-90° C.;
2) at a transmembrane pressure in the range 1.0-3.0 MPa;
3) at a viscosity of not more than 10 mPas.

In an embodiment of the method of the invention, the molecular weight of the degradation products of the composition which is catalytically active in hydroformylation which have been separated off via the permeate does not exceed 400 g/mol and is 20-50% of the molecular weight of the organophosphorus compound used.

In an embodiment of the method of the invention, the retention of the degradation products of the composition which is catalytically active in hydroformylation in the retentate is 80% or less, particularly preferably 70% or less and in particular 50% or less.

Nanofiltration is a pressure-driven membrane separation process. The molecular weight cut-off (MWCO) is in the range from 150 g/mol to 2000 g/mol. This value enables nanofiltration to be distinguished from other membrane separation processes such as microfiltration and ultrafiltration. The molecular weight cut-off is defined as the molar mass of a preferred inert indicator system (e.g. polystyrene standards or alkane standards, cf. Y. H. See Toh, X. X. Loh, A. Bismarck, A. G. Livingston, In search of a standard method for the characterisation of organic solvent nanofiltration membranes, J. Membr. Sci, 291(2007)120-125) at which a membrane has a retention of 90%.

The precise molecular weight cut-off of a nanofiltration membrane is determined by the membrane used and the respective solvent and also by the process conditions such as pressure and temperature.

The molecular weight cut-offs thus sometimes differ greatly for different solvents. In the following, the molecular weight cut-offs mentioned are based on a determination in toluene using polystyrene standards at 30° C. and a transmembrane pressure difference of 3.0 MPa as described by Y. H. See Toh, X. X. Loh, A. Bismarck, A. G. Livingston, [In search of a standard method for the characterisation of organic solvent nanofiltration membranes], J. Membr. Sci, 291(2007)120-125).

In a particular embodiment of the method of the invention, the membrane filtration has, at least at one point, a retention of 90% at a temperature of 30° C. and a transmembrane pressure of 3.0 MPa in toluene in the range from 400 g/mol to 500 g/mol and, at least at one point, a retention of 60% in the range from 210 g/mol to 310 g/mol.

Dense or porous membranes are used in nanofiltration. Nanofiltration membranes display low retention for low molecular weight organic materials.

The retention R of a membrane is determined by the local concentrations of a component i of the stream which does not permeate (retentate) and of the stream which permeates with the membrane (permeate). If retentate and permeate are ideally mixed along the membrane, the local retentate and permeate concentrations correspond to the respective concentration of the total retentate and permeate, respectively, obtained. The retention R of a membrane for a component i present in the stream fed in is generally defined as follows:

$$R = 1 - cPi/cRi$$

Here, cPi is the concentration of the component i in the permeate P and cRi is the concentration of the component i in the retentate R. In the limiting case of complete retention of the component i by the membrane, cPi=0 and R=1. In the case of preferential permeation of the component i, cPi>cRi and R<0.

Preference is given to using membranes which have a separation-active layer of materials selected from among cellulose acetate, cellulose triacetate, cellulose nitrate, regenerated cellulose, polyimides, polyamides, polyether ether ketones, sulphonated polyether ether ketones, aromatic polyamides, polyamidimides, polybenzimidazoles, polybenzimidazolones, polyacrylonitrile, polyaryl ether sulphones, polyesters, polycarbonates, polytetrafluoroethylene, polyvinylidene fluoride, polypropylene, polydimethylsiloxane, silicones, polyphosphazenes, polyphenyl sulphides, polybenzimidazoles, 6.6 Nylon, polysulphones, polyanilines, polypropylenes, polyurethanes, acrylonitrile-glycidyl methacrylate (PANGMA), polytrimethylsilylpropynes, polymethylpentynes, polyvinyltrimethylsilane, polyphenylene oxide, γ-aluminium oxides, α-aluminium oxides, titanium doxides, silicon oxides, zirconium oxides, silane-hydrophobized ceramic membranes as are described in DE 103 08 111, polymers having intrinsic microporosity (PIM) such as PIM-1 and others, as are described, for example, in EP 0 781 166, WO 2010/097376 A1 and in "Membranes" by I. Cabasso, Encyclopedia of Polymer Science and Technology, John Wiley and Sons, New York, 1987.

The abovementioned materials can, in particular, optionally be present in crosslinked form in the separation-active layer as a result of addition of auxiliaries or, as "mixed matrix membranes", be provided with fillers such as carbon nanotubes, metal organic frameworks or hollow spheres or particles of inorganic oxides or inorganic fibres, e.g. ceramic fibres or glass fibres.

Particular preference is given to using membranes which have a polymer layer of polydimethylsiloxane, polyimide, polyamidimide, acrylonitrile-glycidyl methacrylate (PANGMA), silicone acrylate, terminally or laterally organomodified siloxane, polyamide or polyether ether ketone as separation-active layer and are made up of polymers having intrinsic microporosity (PIM) such as PIM-1, or in which the separation-active layer is built up on a hydrophobicized ceramic membrane. Very particular preference is given to using membranes composed of silicones or polyamidimide. Such membranes are commercially available.

In a further embodiment of the apparatus of the invention, the material of the nanofiltration membrane is selected from among:
a) polydimethylsiloxane;
b) silicone acrylate; acrylate;
c) terminally and/or laterally organomodified siloxane;
d) polyimide;
e) PIM-1.

Apart from the abovementioned materials, the membranes can comprise further materials. In particular, the membranes can have support or carrier materials to which the separation-active layer has been applied. In such composite membranes, a support material is present in addition to the actual membranes. A selection of support materials is described in EP 0 781 166, which is explicitly incorporated by reference.

A selection of commercially available organic solvent nanofiltration membranes are the MPF and Selro series from Koch Membrane Systems, Inc., various types of Solsep BV, the Starmem™ series from Grace/UOP, the DuraMem™ and PuraMem™ series from Evonik Industries AG, the Nano-Pro series from Bio-Pure Technology, HITK-T1 from IKTS, and also oNF-1, oNF-2 and NC-1 from GMT Membrantechnik GmbH.

The nanofiltration device used in the method of the invention and the apparatus of the invention particularly preferably comprises one or more nanofiltration membranes, with at least one of the nanofiltration membranes having a molecular weight cut-off in the range from 150 to 2000 g/mol, preferably from 200 to 600 g/mol, particularly preferably from 350 to 500 g/mol.

The membranes are preferably used in the form of membrane modules in the method of the invention. In these modules, the membranes are arranged so that flow can occur over the retentate side of the membrane in such a way that the concentration polarization of the components separated off, here catalyst-ligand system, is countered and moreover, the necessary driving force or pressure can be applied. The permeate is combined in the permeate collection space on the permeate side of the membrane and discharged from the module. Customary membrane modules have the membranes in the form of membrane discs, membrane cushions or membrane bags. In the method of the invention, the membranes are preferably used in the form of membrane modules having open-channelled cushion module systems in which the membranes are thermally fused or adhesively bonded to form membrane bags or cushions or open-channelled (wide-spacer) wound modules in which the membranes are adhesively bonded or fused to form membrane bags or membrane cushions and are wound up together with feed spacers around a permeate collection tube.

Flow over the membrane, separation step

To avoid deposits on the membrane, particular flow conditions have to be adhered to within the membrane separation steps. It has been found that the risk posed by deposits to a stream depends on its turbulence and thus on its Reynolds number. Thus, depending on the construction of the membrane module, it has to be ensured that the Reynolds number is in the range from 55 to 13 500, preferably from 100 to 3500 and very particularly preferably from 170 to 900. The viscosity should at the same time be less than 10 mPas and preferably be 1 mPas. Deposits are avoided under these flow conditions.

The dimensionless Reynolds number Re is defined as Re=w·dh/v, where v is the kinematic viscosity, w is the average velocity of flow over the membrane and dh is the hydraulic diameter as characteristic length of the membrane module. The determination of the hydraulic diameter for spiral wound elements is described in G. Schock et al. "Mass transfer and pressure loss in spiral wound modules", Desalination, 64 (1987) 339-352.

To implement these flow conditions, the method is preferably carried out, when using wound membranes having a tube length of 1 m and a pressure drop of 0.15 MPa and a kinematic viscosity of the medium of 1 mPas, in such a way that the membrane separation step, in particular the first membrane separation step, has a velocity of flow over the membrane of from 0.1 to 15 m/sec., preferably from 0.2 to 4 m/sec., more preferably from 0.3 to 1 m/sec, in order to avoid deposits on the membrane.

The method of the invention is preferably carried out with the solution to be separated being fed as feed stream to the membrane and the retentate stream being partly recirculated to the membrane. Here, the substream which is recirculated to the membrane is firstly combined with the solution to be separated. The part of the retentate stream which is not recirculated to the membrane is either used as feed stream for one or more subsequent separation stages or else recirculated to the reaction.

If a stream having a low proportion of high boilers and a high proportion of primary products, as is the case for a reactor output without prior concentration of high boilers, is fed to the membrane separation step, the volume flow ratio of permeate stream to feed stream from the reactor (without recirculated retentate) is from 1:1.1 to 1:5, preferably from 1:1.4 to 1:3 and particularly preferably from 1:1.6 to 1:2.

If, conversely, a stream which has been significantly enriched in high boilers, compared to the reactor output, downstream of the reactor, e.g. by means of a thermal separation step, is fed to the membrane separation step, the volume flow ratio of permeate stream to feed stream from the reactor (without recirculated retentate) is preferably from 1:5 to 1:20, more preferably from 1:7.5 to 1:12.5 and particularly preferably from 1:9 to 1:11.

It can be advantageous for the volume flow passed over the membrane to be significantly greater than the volume flow of the permeate stream since a high velocity of flow over the membrane can be set in this simple way. The volume flow ratio of the stream fed to the membrane, in particular to the first membrane of the first membrane separation step, (flow from the reactor including recirculated retentate) to permeate flow is preferably 10-10 000:1, more preferably 50-5000:1 and particularly preferably 200-2000:1. Thus, a relatively high volume flow is preferably circulated over the membrane. The size of the part of the retentate stream which is recirculated to the reaction or fed to a further separation is given by the difference between feed stream (without recirculated retentate) and permeate stream.

In the case of relatively high permeabilities, it can also be advantageous to arrange the membranes in a fir-tree structure.

As feed stream to the membrane separation, it is possible to use the reaction output from a reaction catalyzed by organic metal complexes, either directly or as a concentrate produced therefrom. The reaction outputs contain starting materials, primary products, by-products such as ligand degradation products, the composition which is catalytically active in hydroformylation and possibly a solvent. When this mixture is worked up according to the invention, the catalytically active composition, in particular the metal complex, remains predominantly in the retentate. Starting materials, products and ligand degradation products are separated off together with the permeate, which is worked up in a further separation stage. In this case, the permeate stream is significantly larger than the retentate stream which is not recirculated to the membrane. This requires a large membrane area and suboptimal retention of the catalytically active composition.

DESCRIPTION OF THE APPARATUS OF THE INVENTION AND THE METHOD

An embodiment of the apparatus of the invention is depicted in FIG. 1.

The plant consists of three reactors (A1 to A3). The liquid starting material (1), the synthesis gas (2), optionally fresh ligand solution or catalyst solution (15) and the catalyst recycle stream from the nanofiltration (6) are fed into the first reactor (A1). The reactors (A1 to A3) are connected to one another via a two-way gas line (10). The liquid phase is conveyed via an overflow in the top region of each reactor to the bottom of the next reactor (12). At the overflow of the last reactor (A3), the liquid product stream (8) is fed to the stripping vessel (B1). The stripping vessel (B1) can be heated via a double wall and an internal coiled tube. The temperature in the stripping vessel (B1) can be in the range from 80° C. to 140° C. The pressure in the stripping vessel (B1) can be in the range from 5 bar to 17 bar. The offgas stream from the reactors (A1 to A3) is fed under pressure regulation to the stripping vessel (B1).

Here, the offgas stream (14) can optionally firstly be combined with the product stream (8), be fed separately into the stripping vessel (B1) (broken line) or else be fed to the bottom of the stripping vessel (B1) (broken line). The reactors (A1 to A3) have separate facilities for heating or cooling.

For this purpose, the reactors are equipped with a double wall and additional internal coiled tubes.

From the stripping vessel (B1), the gas phase (7) is conveyed via a condenser (B2). Here, a major part of the condensable components is condensed out from the gas stream and separated in the phase separation vessel (B3). The liquid phase (5) from the phase separation vessel (B3) is passed to further work-up.

The gas phase (11) from the phase separation vessel (B3) is fed to a compressor (B4) which recirculates the gas stream (9) back to the bottom of the stripping vessel (B1) in order to allow separation of product and catalyst stream under superatmospheric pressure. The excess gas (3) is discharged from the system under pressure regulation and passed to a further use.

Figure 3:
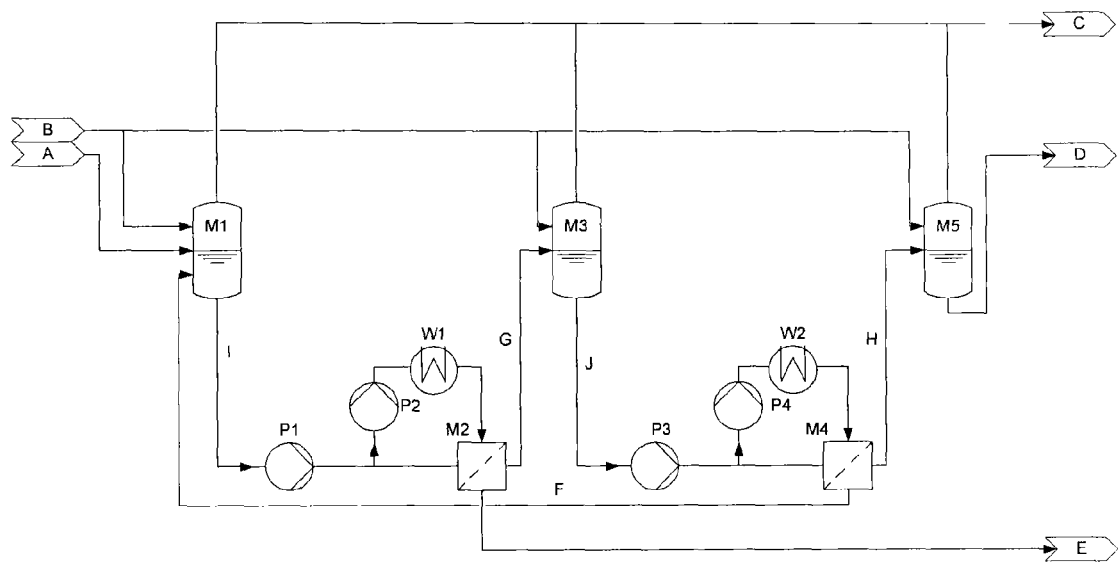
FIG. 3 is a schematic diagram of an embodiment of the apparatus of the invention.

The bottom stream (13) from the stripping vessel (B1) is brought back to the reaction pressure in the reactors (A1 to A3) by means of a pump and fed to the nanofiltration (C1), as shown in FIG. 3. Here, the stream is divided into the catalyst recycle stream (6) and the discharge stream (4). The discharge stream (4) is passed to a further work-up.

Method and Apparatus Alternatives

Figure 4:
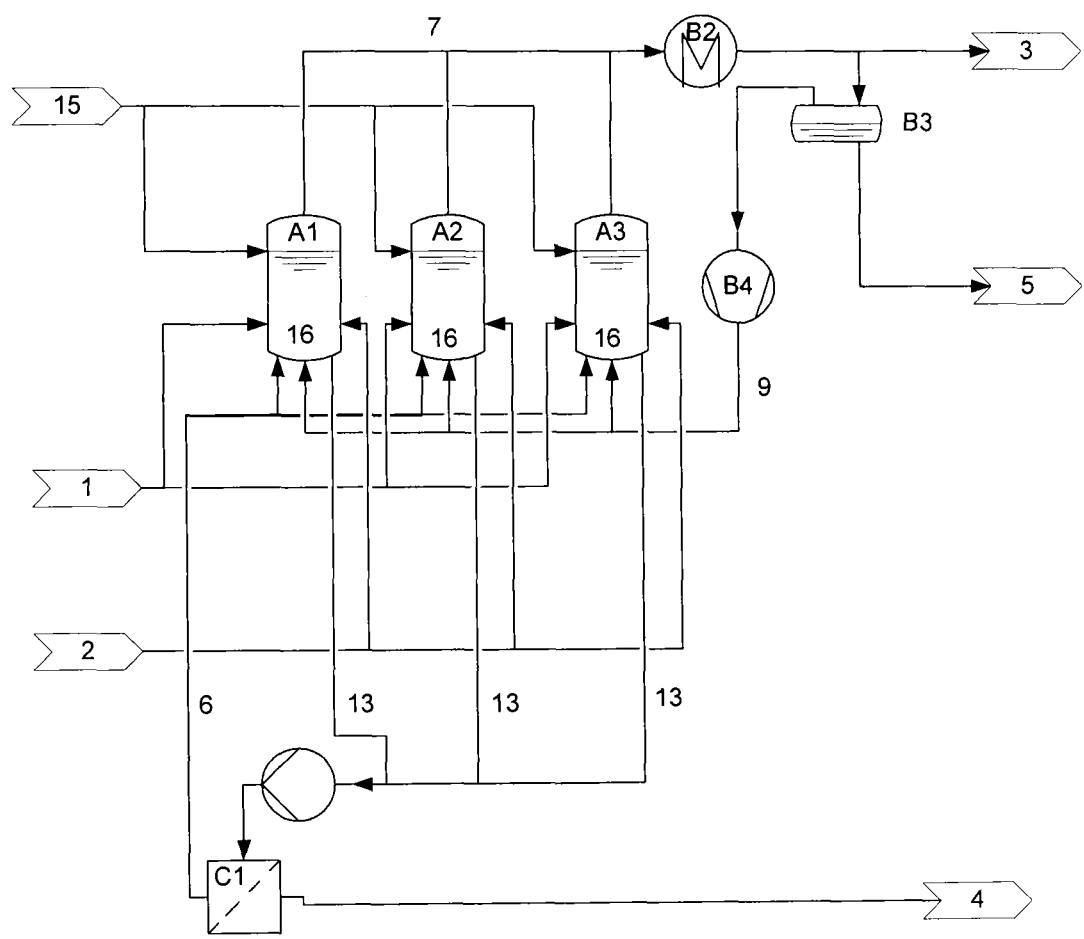
FIG. 4 is a schematic diagram of an embodiment of the apparatus of the invention.

A further embodiment of the apparatus of the invention is shown in FIG. 4. The plant consists of three reactors (A1 to A3). The starting material (1), in liquid or gaseous form, the synthesis gas (2), optionally fresh ligand solution or catalyst solution (15) and the catalyst recycle stream from the nanofiltration (6) are fed into each of the reactors (A1 to A3). The product is removed from the reactors (A1 to A3) via a recycle gas stream which removes the product from the reaction mixture according to the partial pressure fraction. For this purpose, a recycle gas stream (9) is fed via the compressor (B4) into the bottom of each of the reactors (A1 to A3). The product-saturated gas (7) leaves the reactors at the top and is fed to a condenser (B2). Here, the product-saturated gas is cooled and the product partially condenses out. The product is collected in vessels (B3) and passed to further work-up. Excess gas is removed from the system via a pressure regulator (3).

A substream of the reaction solution is taken (13) from each reactor and fed to the nanofiltration plant (C1), as shown in FIG. 3. The resulting permeate stream (4) is passed to a further work-up. The retentate stream (6) is fed back to the reactors (A1-A3).

In an embodiment of the apparatus of the invention, the condensation zone which comprises a heat exchanger or condenser B(2) and a collection vessel B(3) is combined in one structural component.

EXAMPLES

Abbreviations acac=acetylacetonate

Experimental Description—General

The experiments were carried out in 500 ml autoclaves from Parr Instrument. The autoclaves are equipped with electric heating. The pressure is kept constant by means of mass flow meters and pressure regulators. Samples can be taken via capillary lines and HPLC valves during the time of the experiment and be examined both by means of GC analysis and LC-MS analysis.

The solvents were dried over suitable desiccants before use. (Purification of Laboratory Chemicals, W. L. F. Armarego (Author), Christina Chai (Author), Butterworth Heinemann (Elsevier), 6$^{th}$ Edition, Oxford 2009).

In order to demonstrate the relationships between the viscosity of the reaction solution and the compounds present therein and also their contents, Examples I to XI below were carried out.

It is known from the prior art, as disclosed, for example, in EP 1 430 014 B1, that the viscosity of compositions is made up to a good approximation by the individual components of the solution to be examined according to their proportion in this solution. This applies to systems which display Newtonian behaviour.

Example XI is based on the prior art disclosed in WO 2010/003073 A1 and serves as comparative example.

Example I

In a 500 ml autoclave which had been made inert by means of argon, 200 ml of aldehydes having a composition of 5% of 2-methylbutanal and 95% of pentanal, were subject to a temperature of 120° under 1.7 MPa of a CO/H$_2$ (50% by volume/50% by volume) atmosphere. A 4 ml sample was taken in each case from the autoclave and the viscosity was measured. The amount of sample taken was replaced by aldehyde. The aldehyde has the same composition as the aldehyde used at the beginning. After 1800 hours, the experiment was stopped and the aldehyde conversion was determined by GC. The conversion of the C5 aldehydes was 95%. The analysis showed that the aldehydes had been converted into high boilers. The main product was the condensed product of the corresponding C10-aldols. On emptying the autoclave, an aqueous phase was found.

(The decrease in viscosity can be explained by the condensation of the aldol products. After 650 hours, a viscosity of 14 mPas was measured, corresponding to the viscosity of the uncondensed aldol products. Subsequent elimination of water forms the C10-enal, resulting in a decrease in viscosity in this experiment.)

TABLE 001

| Time in h | Viscosity in mPas |
|---|---|
| 0 | 0.5 |
| 650 | 14 |
| 1000 | 8 |
| 1200 | 5 |
| 1400 | 2 |
| 1500 | 2 |
| 1700 | 2 |

Example II

In a 500 ml round-bottom flask provided with reflux condenser and water separator, 200 ml of aldehydes having a composition of 95% of pentanal and 5% of 2-methylbutanal were refluxed under atmospheric pressure in an argon atmosphere. Water formed was removed from the system at the water separator.

A 4 ml sample was taken in each case from the apparatus and the viscosity was measured. The amount of sample taken was replaced by aldehyde. The aldehyde has the same composition as the aldehyde used at the beginning. After 1150 hours, the experiment was stopped and the aldehyde conversion was determined by GC.

The conversion of the C5 aldehydes was 95%.

The analysis showed that the aldehydes had been converted into high boilers. The main product was the tetrameric product of the C5-aldehyde. The condensed product found in Example 1 was detected only in the low percentage range.

TABLE 002

| Time in h | Viscosity in mPas |
|---|---|
| 0 | 0.5 |
| 180 | 7 |
| 600 | 7 |
| 800 | 6 |
| 1000 | 7 |
| 1150 | 6 |

Since the corresponding high boilers of the aldehydes are obviously not responsible for a rise in viscosity, various derivatives apart from the phenols ([1,1'-biphenyl]-2,2'-diol and 3,3'-di-tert-butyl-5,5'-dimethoxy-[1,1'-biphenyl]-2,2'-diol) formed from the ligand 5 b, also known under the abbreviation biphephos or as 6,6'-((3,3'-di-tert-butyl-5,5'-dimethoxy-[1,1'-biphenyl]-2,2'-diyl)bis(oxy))-bis-dibenzo[d,f][1,3,2]dioxaphepine) were examined to determine their influence on the viscosity of the reaction mixture.

These biphenol derivatives can be used in a known way for the synthesis of phosphite ligands.

The stabilizer used in Examples XI, XII and XIII was likewise examined to determine its influence on the viscosity.

Example III

Solutions of 2,2'-dihydroxybiphenyl, viz. component A of the ligand degradation products, were in each case made up in Texanol (2,2,4-trimethyl-1,3-pentanediol monoisobutyrate), viz. the trimeric addition product of the C4-aldehydes as per CAS Reg. No. 25265-77-4, and the viscosity of the solution at room temperature was measured.

TABLE 003

| 2,2'-Dihydroxybiphenyl w % in Texanol | Viscosity in mPas |
|---|---|
| 0 | 17 |
| 2 | 20 |
| 3 | 22 |
| 6 | 25 |
| 10 | 32 |
| 20 | 78 |

Example IV

Solutions of bis(2,2,6,6-tetramethyl-4-piperidinyl) sebacate were in each case made up in Texanol, viz. the trimeric addition product of the C4-aldehydes as per CAS Reg. No. 25265-77-4, and the viscosity of the solution was measured at room temperature.

TABLE 004

| Bis (2,2,6,6-tetramethyl-4-piperidinyl) sebacate w % in Texanol | Viscosity in mPas |
| --- | --- |
| 0 | 17 |
| 2 | 19 |
| 5 | 21 |
| 10 | 30 |
| 20 | 44 |

Example V

The solubility limit of 3,3'-di-tert-butyl-5,5'-dimethoxy-[1,1'-biphenyl]-2,2'-diol, viz. component B of the ligand degradation products, in Texanol, viz. the trimeric addition product of the C4-aldehydes as per CAS Reg. No. 25265-77-4, was determined by means of HPLC analysis. For this purpose, 5 g of 3,3'-di-tert-butyl-5,5'-dimethoxy-[1,1'-biphenyl]-2,2'-diol were added at room temperature to 50 g of Texanol while stirring. The solution was stirred overnight. On the next morning, the solution was still turbulent. After the stirrer had been switched off, a sediment formed. A sample of the supernatant clear solution was taken and analysed by HPLC. The analysis indicated that 0.4 g/l of 3,3'-di-tert-butyl-5,5'-dimethoxy-[1,1'-biphenyl]-2,2'-diol was present in the solution. The sediment was filtered off from the mixture and dissolved in THF. A sample of this solution was analysed by GC-MS and indicated that the solid was 3,3'-di-tert-butyl-5,5'-dimethoxy-[1,1'-biphenyl]-2,2'-diol.

Example VI

Solutions of 3,3',5,5'-tetramethyl-[1,1'-biphenyl]-2,2'-diol were in each case made up in Texanol as per CAS Reg. No. 25265-77-4, viz. the trimeric addition product of the C4-aldehydes, and the viscosity of the solution at room temperature was measured.

TABLE 005

| 3,3',5,5'-Tetramethyl-[1,1'-biphenyl]-2,2'-diol w % in Texanol | Viscosity in mPas |
| --- | --- |
| 0 | 14 |
| 2 | 15 |
| 5 | 17 |
| 10 | 21 |
| 20 | 35 |

Example VII

Solutions of 2,4-dimethylphenol were in each case made up in Texanol, viz. the trimeric addition product of the C4-aldehydes as per CAS Reg. No. 25265-77-4, and the viscosity of the solution at room temperature was measured.

TABLE 006

| 2,4-Dimethylphenol w % in Texanol | Viscosity in mPas |
| --- | --- |
| 0 | 14 |
| 2 | 14.1 |
| 5 | 14.3 |
| 10 | 15.3 |
| 20 | 17.2 |

Example VIII

The solubility limit of 3,3',5,5'-tetrakis-tert-butyl-[1,1'-biphenyl]-2,2'-diol in Texanol, viz. the trimeric addition product of the C4-aldehydes as per CAS Reg. No. 25265-77-4, was determined by means of HPLC analysis.

For this purpose, 5 g of 3,3',5,5'-tetrakis-tert-butyl-[1,1'-biphenyl]-2,2'-diol were added at room temperature to 50 g of Texanol while stirring. The solution was stirred overnight. On the next morning, the solution was still turbid. After the stirrer had been switched off, a sediment was formed. A sample of the supernatant clear solution was taken and analysed by HPLC. The analysis indicated that 0.4 g/l of 3,3',5,5'-tetrakis-tert-butyl-[1,1'-biphenyl]-2,2'-diol were present in the solution. The sediment was filtered off from the mixture and dissolved in THF. A sample of this solution was analysed by GC-MS and indicated that the solid was 3,3',5,5'-tetrakis-tert-butyl-[1,1'-biphenyl]-2,2'-diol.

Example IX

Solutions of [1,1'-binaphthalene]-2,2'-diol were in each case made up in Texanol, viz. the trimeric addition product of the C4-aldehydes as per CAS Reg. No. 25265-77-4, and the viscosity of the solution at room temperature was measured.

TABLE 007

| [1,1'-Binaphthalene]-2,2'-diol w % in Texanol | Viscosity in mPas |
| --- | --- |
| 0 | 14 |
| 2 | 15 |
| 5 | 16 |
| 10 | 19.5 |
| 20 | 29 |

Example X

Solutions of 2-methyl-4,6-di-tert-butylphenol were in each case made up in Texanol, viz. the trimeric addition product of the C4-aldehydes as per CAS Reg. No. 25265-77-4, and the viscosity of the solution at room temperature was measured.

TABLE 008

| 2-Methyl-4,6-di-tert-butylphenol w % in Texanol | Viscosity in mPas |
| --- | --- |
| 0 | 14 |
| 2 | 14.2 |
| 3 | 15.0 |
| 6 | 16.4 |
| 10 | 19.0 |
| 20 | 26.2 |

SUMMARY

Examples I and II show that no damaging increase in the viscosity occurs during the course of the reaction of the aldehydes used due to their reaction products, as can clearly be seen in the tables Tab001 and Tab002. Thus, these reaction products do not have an adverse effect on the viscosity.

In Examples III, IV, VI, VII, IX, X, the influence of the individual components on the viscosity of the solution is clearly shown in the tables Tab003, Tab004, Tab005, Tab006, Tab007 and Tab008. With increasing concentration of the components, the resulting viscosity of the solution also changes.

In Examples V and VIII, the components displayed an excessively low solubility in the solvent used. Although no viscosity measurements could be carried out here, this formation of solid is undesirable for carrying out the hydroformylation reaction.

Example XI

Comparative Example (not According to the Invention)

Figure 2:
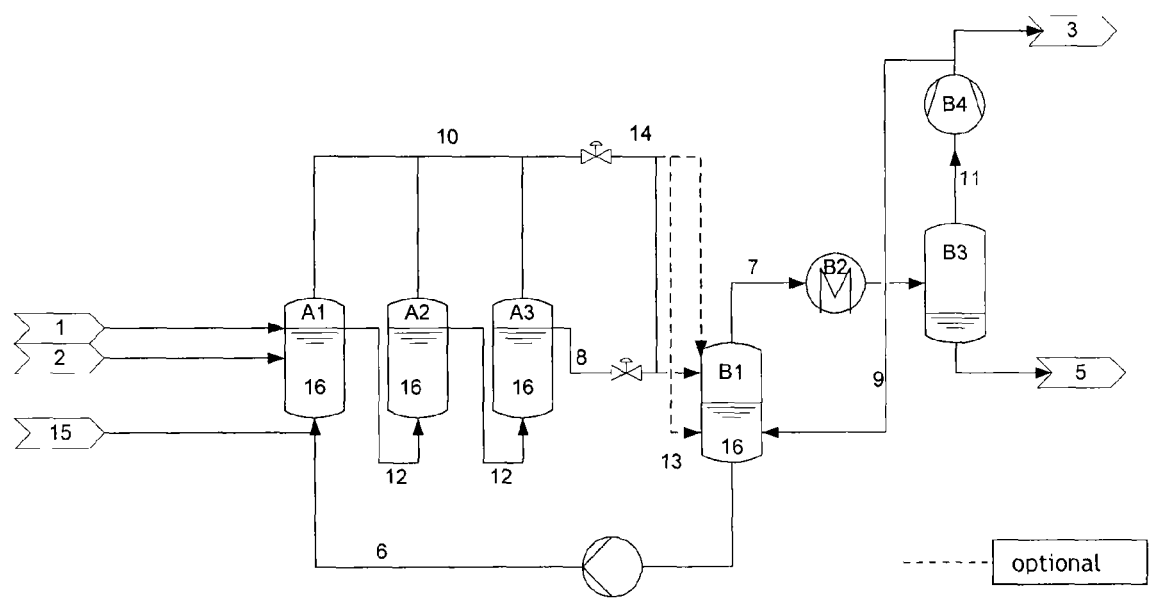
FIG. 2 is a schematic diagram of the plants used in Example XI.

A continuous hydroformylation reaction was carried out using the plants depicted in FIG. 2, based on the prior art of WO 2010/003073 A1.

Here, the reactors were each charged with 7232 g of a catalyst solution. This catalyst solution consisted of 7083 g of isononyl benzoate, 42 g of ligand 5 b, 103 g of bis(2,2, 6,6-tetramethyl-4-piperidinyl) sebacate, 4 g of Rh(acac) $(CO)_2$.

The reactors (A1 to A3) were pressurized with synthesis gas (2) having a composition of 50% by volume of CO and 50% by volume of $H_2$ to 1.7 MPa(abs) and heated to 100° C. The starting material feed stream (1) was then started. 1.9 kg/h of a mixture of from 25% to 32% of 2-butenes in from 75% to 65% of n-butane were introduced into the first reactor (A1). At the same time, synthesis gas (2) having the composition described above was introduced into the first reactor (A1) in order to maintain a reaction pressure of 1.7 MPa(abs). The stripping vessel (B1) was preheated to 120° C. and the condensation temperature in the condenser (B2) was set to 40° C.

The stripping system consisting of the stripping vessel (B1), condenser (B2), phase separation vessel (B3) and compressor (B4) with all connecting lines (14, 7, 9, 11, 13) was pressurized to 1.0 MPa(abs) via the offgas line (14) of the reactors.

For this purpose, the synthesis gas (2) at the first reactor was increased in order to maintain the reaction pressure at 1.7 MPa(abs).

On reaching the overflow in the third reactor (A3), the liquid phase was conveyed via the level regulator (8) into the stripping vessel (B1).

At the same time, the synthesis gas stream (2) was brought to a 1.1-fold molar excess relative to the butene stream (1). The excess gas was conveyed via the pressure regulator of the reactors (14) into the stripping vessel (B1) and there discharged from the plant via the pressure regulator in the stripping system (3). The pressure in the reactors (A1 to A3) was in this way maintained at 1.7 MPa(abs) and that in the stripping system (B1 to B4) was maintained at 1.0 MPa(abs).

When a level of 20% was reached in the stripping vessel (B1), the compressor (B4) was started and the product was driven off from the liquid phase by means of the gas stream (9) produced. The gas stream (9) was adapted according to the level in the stripping vessel (B1). When the level in the stripping vessel (B1) increased, the gas stream (9) was increased and when the level in the stripping vessel (B1) dropped, the gas stream (9) was reduced. The amount of gas necessary varied in the range from 300 to 1200 l/h according to the level. A catalyst stream (13) of 900 g/h was recirculated (6) by means of a pump from the bottom of the stripping vessel (B1) to the first reactor (A1).

The conversion in the reactor (A3) was determined by means of GC.

The proportion of unbound ligand in the stripping vessel (B1) was determined by means of HPLC and this was kept constant by introduction of further 2% strength ligand solution in degassed crude product (15). The ratio of unbound ligand 5 b, biphephos for short or (6,6'-((3,3'-di-tert-butyl-5,5'-dimethoxy-[1,1'-biphenyl]-2,2'-diyl)bis (oxy))-bis-dibenzo[d,f][1,3,2]dioxaphosphepine), to rhodium was maintained at a molar ratio of 1:1. This solution contained the ligand 5 b together with bis(2,2,6,6-tetramethyl-4-piperidinyl) sebacate in a molar ratio of bis(2,2,6,6-tetramethyl-4-piperidinyl) sebacate to ligand 5 b, biphephos for short or (6,6'-((3,3'-di-tert-butyl-5,5'-dimethoxy-[1,1'-biphenyl]-2,2'-diyl)bis(oxy))-bis-dibenzo[d,f][1,3,2]dioxaphosphepine) of 2:1.

Apart from the ligand content, the viscosity of the reactor solution in the stripping vessel (B1) was measured.

After about 1500 hours, corresponding to a time on stream of 62.5 days, the level in the stripping vessel (B1) increased and could no longer be reduced by increasing the amount of gas.

Figure 5:
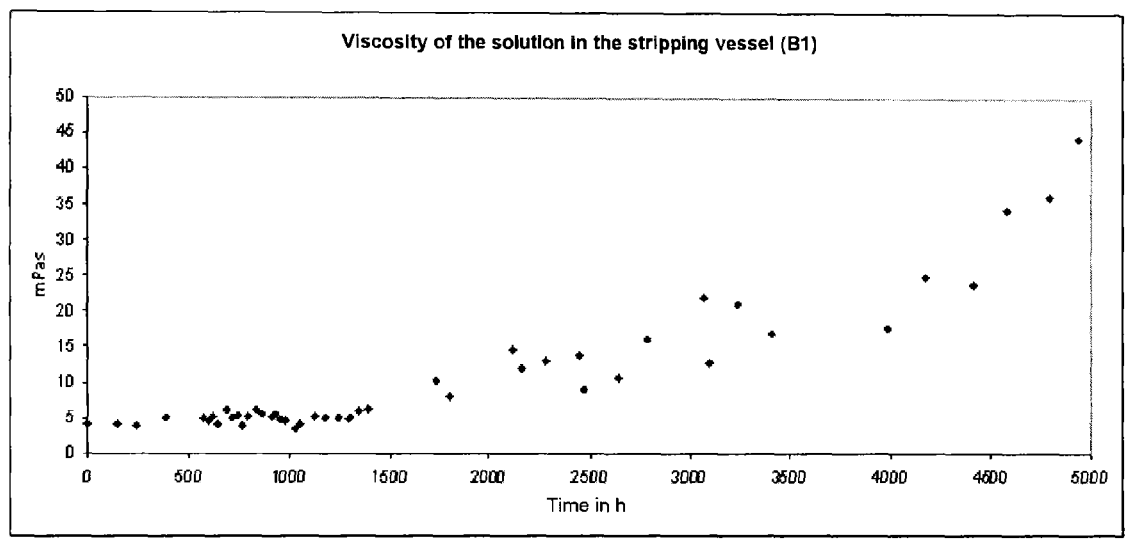
FIG. 5 is a graph showing viscosity of a solution in the stripping vessel (B1).

At the same time, an increase in the viscosity was observed. The experiment was continued to 7500 hours, corresponding to a time on stream of 312.5 days. The viscosity at the end of the time on stream was above 350 mPas and thus displayed an increase by a factor of 70 compared to the initial conditions; see FIG. 5. A decrease in the conversion was observed. A white solid was found on draining the reaction solution from the reaction system.

Example XII

According to the Invention

A continuous hydroformylation reaction was carried out using the plant depicted in FIG. 1. The catalyst solution was made up in a manner analogous to Example XI.

The reactors (A1 to A3) were pressurized with synthesis gas (2) having a composition of 50% by volume of CO and 50% by volume of $H_2$ to 1.7 MPa(abs) and heated to 100° C. The starting material feed stream (1) was then started. 1.9 kg/h of a mixture of from 25% to 35% of 2-butenes in from 75% to 65% of n-butane were introduced into the first reactor (A1). At the same time, synthesis gas (2) having the composition described above was introduced into the first reactor (A1) in order to maintain a reaction pressure of 1.7 MPa(abs). The stripping vessel (B1) was preheated to 120° C. and the condensation temperature in the condenser (B2) was set to 40° C.

The stripping system consisting of the stripping vessel (B1), condenser (B2), phase separation vessel (B3) and compressor (B4) with all connecting lines (14, 7, 9, 11, 13) was pressurized to 1.0 MPa(abs) via the offgas line (14) of the reactors.

For this purpose, the synthesis gas (2) at the first reactor was increased in order to maintain the reaction pressure at 1.7 MPa(abs).

On reaching the overflow in the third reactor (A3), the liquid phase was conveyed via the level regulator (8) into the stripping vessel (B1).

At the same time, the synthesis gas stream (2) was brought to a 1.1-fold molar excess relative to the butene stream (1). The excess gas was conveyed via the pressure regulator of the reactors (14) into the stripping vessel (B1) and there discharged from the plant via the pressure regulator in the stripping system (3). The pressure in the reactors (A1 to A3) was in this way maintained at 1.7 MPa(abs) and that in the stripping system (B1 to B4) was maintained at 1.0 MPa(abs).

When a level of 20% was reached in the stripping vessel (B1), the compressor (B4) was started and the product was driven off from the liquid phase by means of the gas stream (9) produced. The gas stream (9) was adapted according to the level in the stripping vessel (B1). When the level in the stripping vessel (B1) increased, the gas stream (9) was increased and when the level in the stripping vessel (B1) dropped, the gas stream (9) was reduced. The amount of gas necessary varied in the range from 300 to 1200 l/h according to the level. From the bottom of the stripping vessel (B1), a stream (13) of 900 g/h was conveyed by means of a pump to the two-stage nanofiltration unit (FIG. 3) via the feed line (A) into the reservoir (M1). There, the solution was blanketed with synthesis gas (B) and the pressure above the liquid was maintained at 1.0 MPa(abs). Excess gas was discharged under pressure regulation into the offgas (C). The synthesis gas used has the same composition as the synthesis gas used for the reaction. An amount of synthesis gas of 45 standard l/h was introduced into the reservoir (M1).

From the reservoir (M1), the liquid phase was conveyed under level regulation to the first membrane stage. The membrane stage consisted of the pressurization pump (P1), the stream pump (P2), the heat exchanger (W1) and the flood channel module (M2). The flow over the membrane was set to 300 l/h by means of the pump (P2). The temperature in the first membrane stage was set by means of the heat exchanger (W1) so that retentions of the ligand degradation products, component A and component B, in the range from 10% to 70% were established over the membrane (M2). Here, the transmembrane pressures ranged from 1.0 to 3.0 Mpa.

The retentions of the degradation components, component A and component B, were determined by sampling and HPLC analysis of the retentate stream (E) and of the permeate stream (G). The temperature range in the membrane stage was for this purpose set to from 20° C. to 90° C.

The retentate stream (E) from the first membrane stage was recirculated (6) to the first reactor (A1). Here, a stream of 800-850 g/h was established. The permeate stream (G) from the first membrane stage was fed into the reservoir (M3) of the second membrane stage. This reservoir (M3) was likewise blanketed with synthesis gas pressure in a manner analogous to the first reservoir (M1). An amount of synthesis gas of 40 standard l/h was introduced into the reservoir (M3).

The liquid phase from the reservoir (M3) was likewise conveyed under level control into the second membrane stage. The second membrane stage consisted of the pressurization pump (P3), the stream pump (P4), the heat exchanger (W2) and the flat channel module (M4).

The flow over the membrane was set to 300 l/h by means of the pump (P4).

The retentions of the degradation components, component A and component B, were determined by sampling and HPLC analysis of the retentate stream (E) and of the permeate stream (G). The temperature range in the membrane stage was for this purpose set to from 20° C. to 90° C.

The retentate stream (F) from the second membrane stage was recirculated to the reservoir (M1) of the first membrane stage. The permeate (H) from the second stage was fed into the reservoir (M5) which was likewise blanketed with synthesis gas. From this reservoir (M5), the liquid phase (D) was discharged from the system. This stream amounted to from 50 to 100 g/h.

As membranes, use was made of the PDMS-/polydimethylsiloxane-based type oNF2 from GMT.

Figure 6:
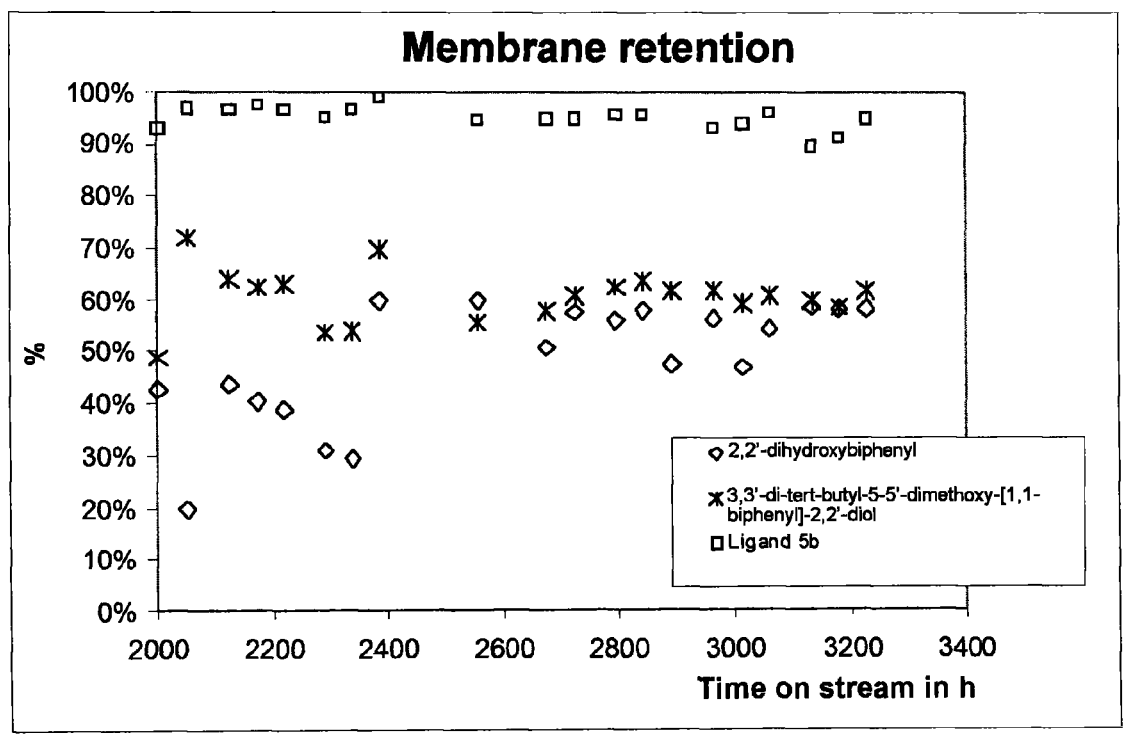
FIG. 6 is a graph showing membrane retention vs. time.

The nanofiltration was operated in such a way that the degradation products of the ligand 5 b, biphephos for short or (6,6'-((3,3'-di-tert-butyl-5,5'-dimethoxy-[1,1'-biphenyl]-2,2'-diyl)bis(oxy))-bis-dibenzo[d,f][1,3,2]dioxaphosphepine), component A and component B, could not accumulate in the system; see FIG. 6.

The retention is calculated as follows:

Retention in %=(1−concentration of the component in the permeate)/concentration of the component in the retentate.

The concentrations are in each case in g/l.

The conversion in the reactor (A3) was determined by means of GC.

The proportion of the ligand in the stripping vessel (B1) was determined by means of HPLC and this was kept at a constant level by introduction of further 2% strength ligand solution in degassed crude product (15). This solution contained the ligand 5 b, biphephos for short or (6, 6'4(3,3'-di-tert-butyl-5,5'-dimethoxy-[1, 1'-biphenyl]-2,2'-diyl)bis(oxy))-bis-dibenzo[d,f][1,3,2]dioxaphosphepine), together with bis(2,2,6,6-tetramethyl-4-piperidinyl) sebacate in a molar ratio of bis(2,2,6,6-tetramethyl-4-piperidinyl) sebacate to the ligand by biphephos (6, 6'4(3,3'-di-tert-butyl-5, 5'-dimethoxy-[1,1'-biphenyl]-2,2'-diyl)bis(oxy))didi-benzo [d,f][1,3,2]dioxaphosphepine) of 2:1.

Apart from the ligand content, the viscosity of the reactor solution in the stripping vessel (B1) was also measured.

Figure 7:
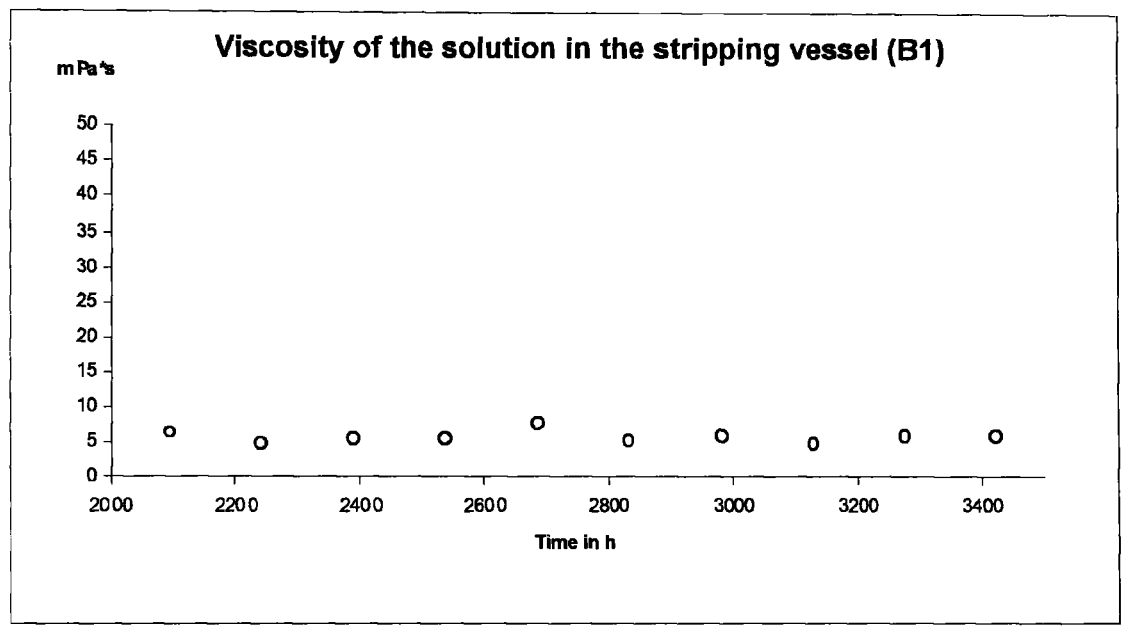
FIG. 7 is a graph showing viscosity of a solution in the stripping vessel (B1).

Even after more than 1800 hours, corresponding to a time on stream of the experiment of 75 days, the level in the stripping vessel (B1) did not increase. In addition, there was no observable increase in the viscosity, see FIG. 7, which remained below 10 mPas during the time of the experiment, and the decrease in conversion which occurred in Example XI was not observed.

After 3500 hours, corresponding to a time on stream of the experiment of 146 days, the reaction system was likewise emptied and no solid could be detected.

Example XIII

According to the Invention

A continuous hydroformylation reaction was carried out using the plant depicted in FIG. 4. Here, the reactors (A1-A3) were each filled with 3690 g of a catalyst solution. This catalyst solution consisted of 3541 g of isononyl benzoate, 42 g of ligand 5 b, 103 g of bis(2,2,6,6-tetramethyl-4-piperidinyl) sebacate, 4 g of Rh(acac)(CO)$_2$.

The reactors (A1 to A3) were pressurized with synthesis gas (2) having a composition of 50% by volume of CO and 50% by volume of H$_2$ to 1.7 MPa(abs) and heated to 100° C. The starting material feed stream (1) was then started. 0.5 kg/h per reactor of a mixture of from 25% to 35% of 2-butenes in from 75% to 65% of n-butane was fed in liquid form into each of the reactors (A1-A3). At the same time, the compressor (B4) was started and the condensation temperature in the condenser (B2) was set to 40° C. The synthesis gas stream (2) was at the same time brought to a 1.1-fold molar excess relative to the butene stream (1).

The excess gas was discharged from the plant via the pressure regulator of the reactors (3). The pressure in the reactors (A1 to A3) was in this way maintained at 1.7 MPa(abs). The gas stream (9) was adapted according to the level in the reactors (A1 to A3). When the level in the reactors (A1 to A3) rose, the gas stream (9) was increased and when the level in the reactors (A1 to A3) dropped, the gas stream (9) was reduced. The amount of gas required varied from 100 to 400 l/h per reactor depending on the level.

From the bottom of the reactors (A1 to A3), a stream (13) of 300 g/h per reactor (A1-A3) was conveyed via a pump to the two-stage nanofiltration unit (FIG. 3) via the feed line (A) into the reservoir (M1). There, the solution was blanketed with synthesis gas (B) and the pressure above the liquid was maintained at 1.0 MPa(abs). Excess gas was discharged under pressure regulation into the offgas (C). The synthesis gas used has the same composition as the synthesis gas used for the reaction. An amount of synthesis gas of 45 standard l/h was introduced into the reservoir (M1).

From the reservoir (M1), the liquid phase was fed under level regulation into the first membrane stage. The membrane stage consisted of the pressurization pump (P1), the stream pump (P2), the heat exchanger (W1) and the flat channel module (M2). The flow over the membrane was set to 300 l/h by means of the pump (P2). The temperature in the first membrane stage was set by means of the heat exchanger (W1) so that the retentions of the ligand degradation products, component A and component B, of from 10% to 70% were established over the membrane (M2). Here, the transmembrane pressures ranged from 1.0 to 3.0 MPa.

The retentions of the degradation products, component A and component B, were determined by sampling and HPLC analysis of the retentate stream (E) and of the permeate stream (G). The temperature range in the membrane stage was for this purpose set in the range from 20° C. to 90° C.

The retentate stream (E) from the first membrane stage was recirculated (6) in equal proportions to the reactors (A1 to A3). A total stream of 800-850 g/h was established here. The permeate stream (G) from the first membrane stage was fed into the reservoir (M3) of the second membrane stage. This reservoir (M3) was likewise blanketed with synthesis gas pressure in a manner analogous to the first reservoir (M1). An amount of synthesis gas of 40 standard l/h was introduced into the reservoir (M3).

The liquid phase from the reservoir (M3) was likewise fed under level regulation into the second membrane stage. The second membrane stage consisted of the pressurization pump (P3), the stream pump (P4), the heat exchanger (W2) and the flat channel module (M4). The flow over the membrane was set to 300 l/h by means of the pump (P4).

The retentions of the degradation components, component A and component B, were determined by sampling and HPLC analysis of the retentate stream (E) and of the permeate stream (G). The temperature range in the membrane stage was for this purpose set to from 20° C. to 90° C.

The retentate stream (F) from the second membrane stage was recirculated to the reservoir (M1) of the first membrane stage. The permeate (H) from the second stage was fed into the reservoir (M5) which was likewise blanketed with synthesis gas. From this reservoir (M5), the liquid phase (D) was discharged from the system. This stream amounted to from 50 to 100 g/h.

As membranes, use was made of the PDMS-/polydimethylsiloxane-based type oNF2 from GMT.

The nanofiltration was carried out in such a way that the degradation products of the ligand 5 b, biphephos for short or (6,6'-((3,3'-di-tert-butyl-5,5'-dimethoxy-[1,1'-biphenyl]-2,2'-diyl)bis(oxy))-bis-dibenzo[d,f][1,3,2]dioxaphosphepine), component A and component B, could not accumulate in the system.

The conversion was determined by means of a gas-phase GC in the inlet stream of the condenser (B2).

The proportion of the ligand was determined by means of HPLC in each reactor (A1 to A3) and this was kept constant by introduction of further 2% strength ligand solution in the degassed crude product (15). This solution contained the ligand 5 b, biphephos for short or (6,6'-((3,3'-di-tert-butyl-5,5'-dimethoxy-[1,1'-biphenyl]-2,2'-diyl)bis(oxy))-bis-dibenzo[d,f][1,3,2]dioxaphosphepine), together with bis(2,2,6,6-tetramethyl-4-piperidinyl) sebacate in a molar ratio of bis(2,2,6,6-tetramethyl-4-piperidinyl) sebacate to the ligand biphephos (6,6'4(3,3'-di-tert-butyl-5,5'-dimethoxy-[1,1'-biphenyl]-2,2'-diyl)bis(oxy))didi-benzo[d,f][1,3,2]dioxaphosphepine) of 2:1.

Apart from the ligand content, the viscosity of the reaction solution in the reactors (A1-A3) was also measured.

Figure 8:
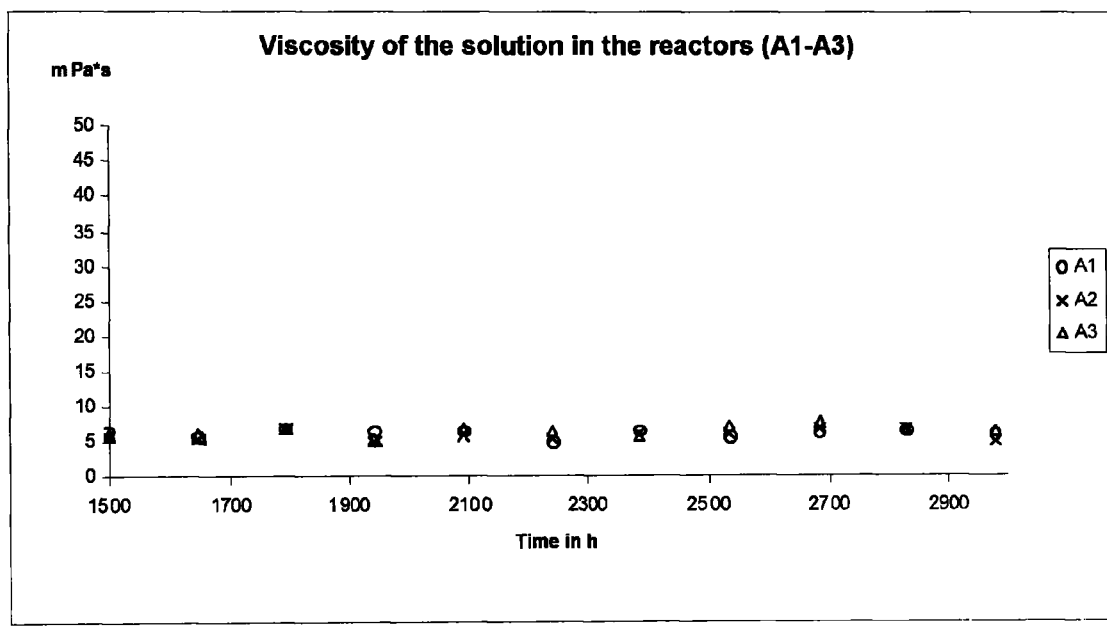
FIG. 8 is a graph showing viscosity of a solution in the reactors (A1-A3).

A rise in level was not found in the reactors even after 3000 hours, corresponding to 125 days, and the viscosity of the reaction solution was, as in Example XII, <10 mPas; see FIG. 8.

LIST OF REFERENCE SYMBOLS (1) Inlet for olefinic compound
(2) Synthesis gas inlet
(3) Offgas (Purge gas)
(4) Permeate from membrane filtration
(5) Crude product
(6) Retentate from membrane filtration
(7) Recycle gas enriched in crude product
(8) Outlet from reaction
(9) Recycle gas inlet
(10) Two-way gas line
(11) Recycle gas depleted in crude product
(12) Reactor overflow
(13) Feed to membrane plant
(14) Pressure regulator
(15) Ligand or catalyst solution
(16) Reaction solution
(B1) Stripping vessel
(B2) Condenser
(B3) Phase separation vessel
(B4) Compressor
(C1) Membrane plant
(A1-A3) Reactors
(C) Offgas with pressure regulator
(M1/M3/M5) Reservoir
(P1/P3) Pressurization pump
(W1/W2) Heat exchanger
(M2/M4) Flat channel module with membrane
(E/F) Retentate stream
(G/H) Permeate stream
(P2/P4) Stream pump
(A) Feed line to membrane plant
(B) Synthesis gas blanketing

The invention claimed is:

1. A method for controlling the viscosity of reaction solutions in the hydroformylation of olefin-containing mixtures, the method comprising:
   i) contacting a mixture comprising saturated and olefinically unsaturated hydrocarbons, a composition which is catalytically active in hydroformylation, a gas mixture comprising carbon monoxide and hydrogen, and at least one solvent, in at least one reaction zone;
   ii) separating off products, with a gas stream comprising a mixture of saturated and olefinically unsaturated hydrocarbons, carbon monoxide and hydrogen being introduced into the at least one reaction zone, with the proviso that the products are discharged via a gas phase from the reaction zone;
   iii) condensing the products which have been separated off via the gas phase and passing them to further work-up; and
   iv) passing a bottom stream from at least one reaction zone to at least one membrane filtration,
   wherein the composition which is catalytically active in hydroformylation is retained in a retentate and recirculated to the at least one reaction zone and degradation products of the composition which are catalytically active in hydroformylation are removed via a permeate.

2. The method of claim 1, wherein the composition which is catalytically active in hydroformylation comprises:
   a) at least one organophosphorus compound comprising trivalent phosphorus;
   b) at least one metal of groups 8-10 of the Periodic Table of the Elements; and
   c) optionally a stabilizing component.

3. The method of claim 2, wherein:
   the organophosphorus compound comprising trivalent phosphorus is selected from the group consisting of a phosphine, a phosphite, a phosphonite, a phospinite, and a phosphoramidite;
   the metal is a group 8 metal of the Periodic Table of the Elements; and
   the composition comprises a stabilizing component which is a sterically hindered amines.

4. The method of claim 3, wherein the metal is rhodium and the sterically hindered amine comprises at least one 2,2,6,6-tetramethylpiperidine unit.

5. The method of claim 1, wherein the degradation products of the composition, which are selected from the group consisting of an alcohol, a phenol, and a diol, are removed via the permeate.

6. The method of claim 5, wherein the membrane filtration is carried out:
   1) in a temperature range of 20-90° C.;
   2) at a transmembrane pressure in the range 1.0-3.0 MPa; and
   3) at a viscosity of not more than 10 mPas.

7. The method of claim 6, wherein a molecular weight of the degradation products which are removed via the permeate does not exceed 400 g/mol and is 20-50% of a molecular weight of the organophosphorus compound.

8. The method of claim 7, wherein the retention of the degradation products in the retentate is 80% or less.

9. The method of claim 8, wherein the membrane filtration has, at least at one point, a retention of 90% at a temperature of 30° C. and a transmembrane pressure of 3 MPa in toluene in the range from 400 g/mol to 500 g/mol and, at least at one point, a retention of 60% in the range from 210 g/mol to 310 g/mol.

* * * * *